United States Patent
Wu et al.

(10) Patent No.: US 10,890,541 B2
(45) Date of Patent: Jan. 12, 2021

(54) GAS DETECTION APPARATUS

(71) Applicant: HTC Corporation, Taoyuan (TW)

(72) Inventors: Chun-Yih Wu, Taoyuan (TW);
Lun-Kang Lin, Taoyuan (TW);
Yen-Liang Kuo, Taoyuan (TW)

(73) Assignee: HTC Corporation, Taoyuan (TW)

( * ) Notice: Subject to any disclaimer, the term of this patent is extended or adjusted under 35 U.S.C. 154(b) by 41 days.

(21) Appl. No.: 16/384,928

(22) Filed: Apr. 16, 2019

(65) Prior Publication Data

US 2019/0339213 A1    Nov. 7, 2019

Related U.S. Application Data

(60) Provisional application No. 62/666,669, filed on May 3, 2018.

(51) Int. Cl.
*G01N 22/00*    (2006.01)

(52) U.S. Cl.
CPC .................... *G01N 22/00* (2013.01)

(58) Field of Classification Search
None
See application file for complete search history.

(56) References Cited

U.S. PATENT DOCUMENTS

| 2008/0219895 | A1* | 9/2008 | Sasaki | G01N 33/006 422/83 |
| 2013/0147493 | A1* | 6/2013 | Marchetti | G01N 33/0036 324/639 |

FOREIGN PATENT DOCUMENTS

| CN | 102636500 | 8/2012 |
| CN | 104303049 | 8/2017 |

OTHER PUBLICATIONS

"Office Action of Taiwan Counterpart Application," dated Oct. 16, 2019, p. 1-p. 5.

* cited by examiner

*Primary Examiner* — Jas A Sanghera
(74) *Attorney, Agent, or Firm* — JCIPRNET

(57) ABSTRACT

A gas detection apparatus including at least one application terminal and at least one equipment terminal is provided. The application terminal sends a plurality of detection electric waves. The equipment terminal is configured to receive a plurality of transmission electric waves respectively generated according to the detection electric waves. The equipment terminal is further configured to calculate a plurality of reference attenuation values of the transmission electric waves in a correction mode; calculate a plurality of detection attenuation values of the transmission electric waves in a monitoring mode; and generate a detection result by comparing the reference attenuation values with the detection attenuation values.

12 Claims, 5 Drawing Sheets

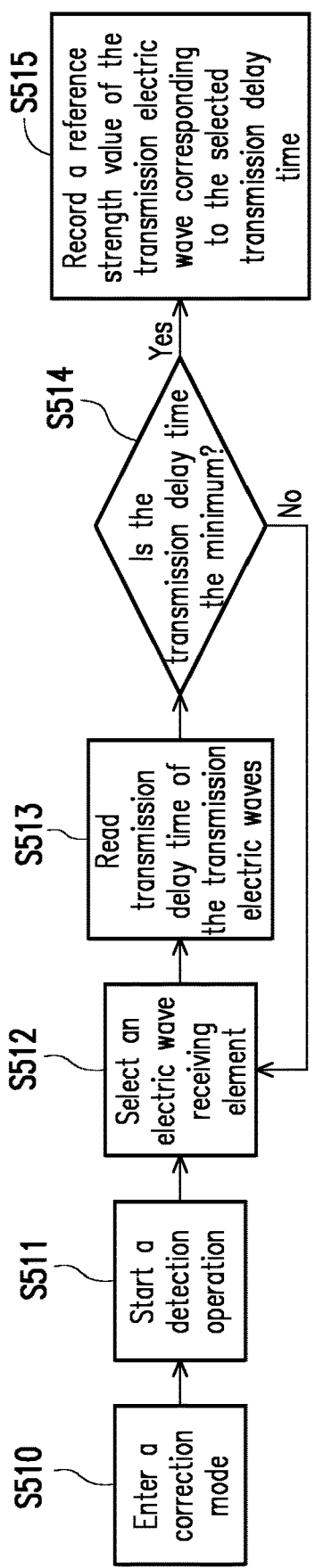
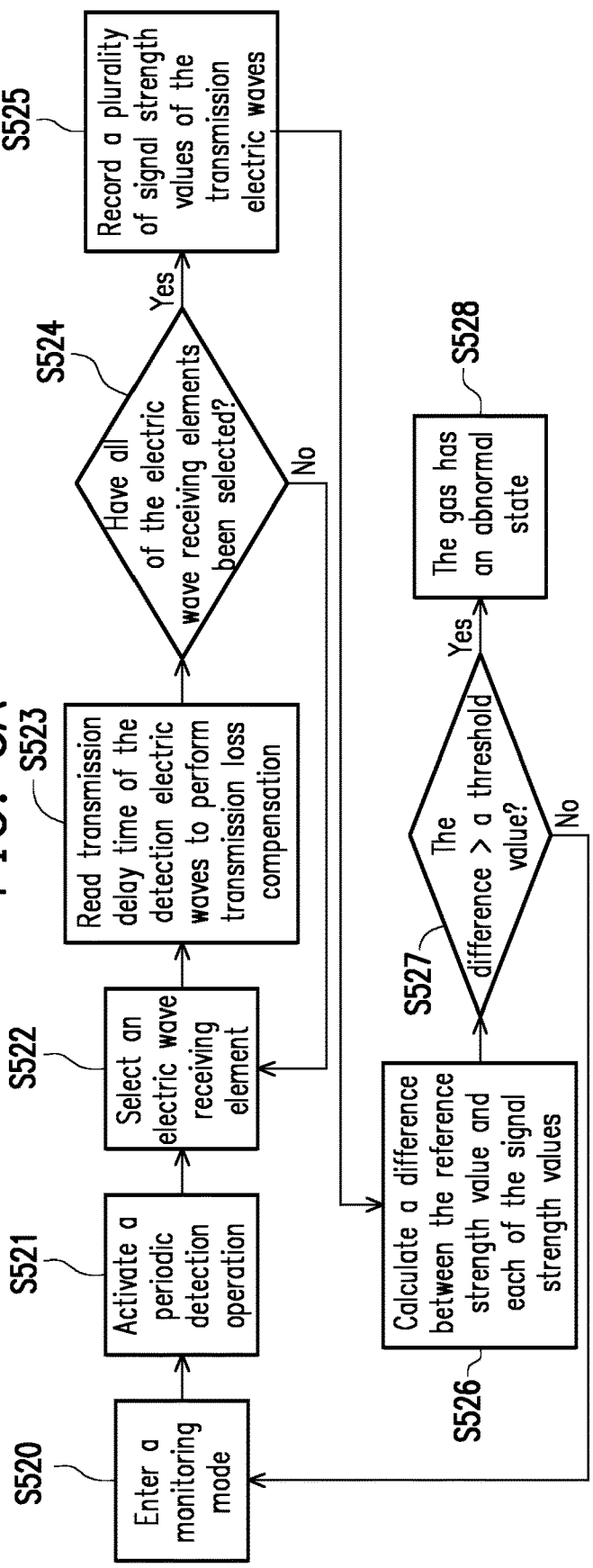
FIG. 5A
FIG. 5B

GAS DETECTION APPARATUS

CROSS-REFERENCE TO RELATED APPLICATION

This application claims the priority benefit of U.S. provisional application Ser. No. 62/666,669, filed on May 3, 2018. The entirety of the above-mentioned patent application is hereby incorporated by reference herein and made a part of this specification.

BACKGROUND

Technical Field

The invention relates to a gas detection apparatus, and particularly relates to an electric wave detection type gas detection apparatus.

Description of Related Art

In a conventional technical field, a state of a gas in a space may be detected to determine whether there is an accident in the space. For example, when an item is burned in the space, a concentration of carbon monoxide in the space rises, and if the state of the gas in the space is detected at this moment, such abnormal state may be learned to send an alarm, so as to avoid expansion of the disaster.

In the conventional technical field, detection of the gas state is often implemented through chemical reaction. Such detection method is often limited to a fixed small range of space, and a response speed of the detection is not high.

SUMMARY

The invention is directed to a gas detection apparatus, which is capable of effectively detecting a gas change state in a space.

The invention provides a gas detection apparatus including at least one application terminal and at least one equipment terminal. The application terminal sends a plurality of detection electric waves. The equipment terminal is configured to receive a plurality of transmission electric waves respectively generated according to the detection electric waves. The equipment terminal is further configured to calculate a plurality of reference attenuation values of the transmission electric waves in a correction mode; calculate a plurality of detection attenuation values of the transmission electric waves in a monitoring mode; and generate a detection result by comparing the reference attenuation values with the detection attenuation values.

The invention provides another gas detection apparatus including at least one application terminal and at least one equipment terminal. The application terminal sends a plurality of detection electric waves. The equipment terminal is configured to receive a plurality of transmission electric waves respectively generated according to the detection electric waves. The equipment terminal is further configured to calculate a plurality of transmission delay times of the transmission electric waves in a correction mode, and calculate the minimum one of the transmission delay time to obtain a selected transmission delay time, and record a reference strength value of the transmission electric wave corresponding to the selected transmission delay time; and calculate and record a plurality of signal strength values of the transmission electric waves in a monitoring mode, and calculate a plurality of differences between the reference strength value and the signal strength values, and generate a detection result according to the differences.

Based on the above description, in the gas detection apparatus of the invention, one or a plurality of application terminals and one or a plurality of equipment terminals are configured in space. The application terminal sends a plurality of detection electric waves, and the equipment terminal receives a plurality of transmission electric waves to learn a strength attenuation of the detection electric waves during a transmission process in the space, and to learn a change state of gas composition in the space according to the obtained strength attenuation. In this way, a real-time gas detection operation may be performed for an unlimited space range, so as to ensure safety of the space.

To make the aforementioned more comprehensible, several embodiments accompanied with drawings are described in detail as follows.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

FIG. 5A and FIG. 5B are flowcharts of a gas detection operation according to another embodiment of the invention.

DESCRIPTION OF THE EMBODIMENTS

Figure 1:
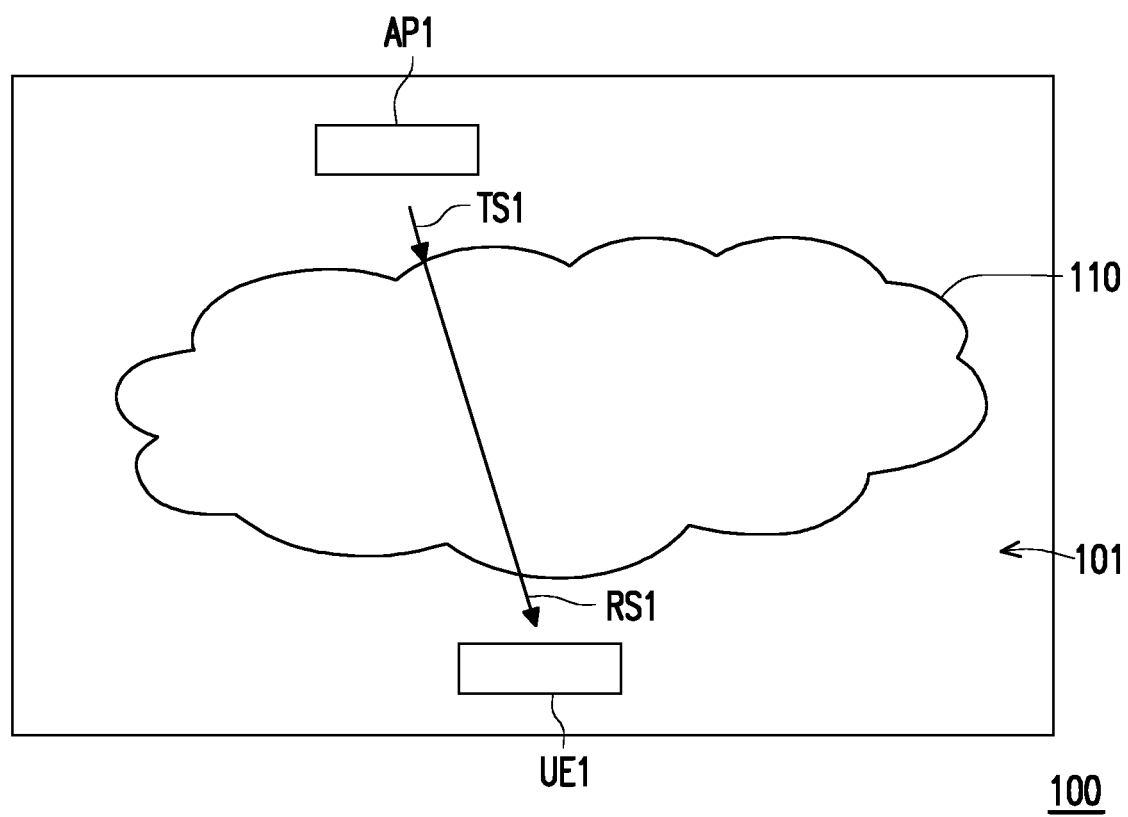
FIG. 1 is a schematic diagram of a gas detection apparatus according to an embodiment of the invention.

Referring to FIG. 1, FIG. 1 is a schematic diagram of a gas detection apparatus according to an embodiment of the invention. The gas detection apparatus 100 includes an application terminal AP1 and an equipment terminal UE1. The application terminal AP1 and the equipment terminal UE1 are commonly disposed in a same space 101. The application terminal AP1 is configured to send a detection electric wave TS1. The equipment terminal UE1 is configured to receive a transmission electric wave RS1 generated according to the detection electric wave TS1. In the embodiment, the application terminal AP1 sends the detection electric wave TS1, and the detection electric wave TS1 penetrate through a medium 110 in the space 101 to generate the transmission electric wave RS1. The medium 110 is a gas in the space 101, and the detection electric wave TS1 may be a radio wave with a frequency of gigahertz (for example, a frequency band of 252-325 GHz of IEEE Std 802.15.3dTM-2017). A gas absorption rate of the detection electric wave TS1 is relatively low, so that a transmission attenuation amount of the detection electric wave TS1 transmitted in the normal gas medium 110 is very small. In contrast, when a composition of the gas becomes abnormal, the transmission attenuation amount of the detection electric wave TS1 transmitted in the medium 110 is abnormally increased to cause reduction of a strength of the transmission electric wave RS1 generated according to the detection electric wave TS1.

Figure 2:
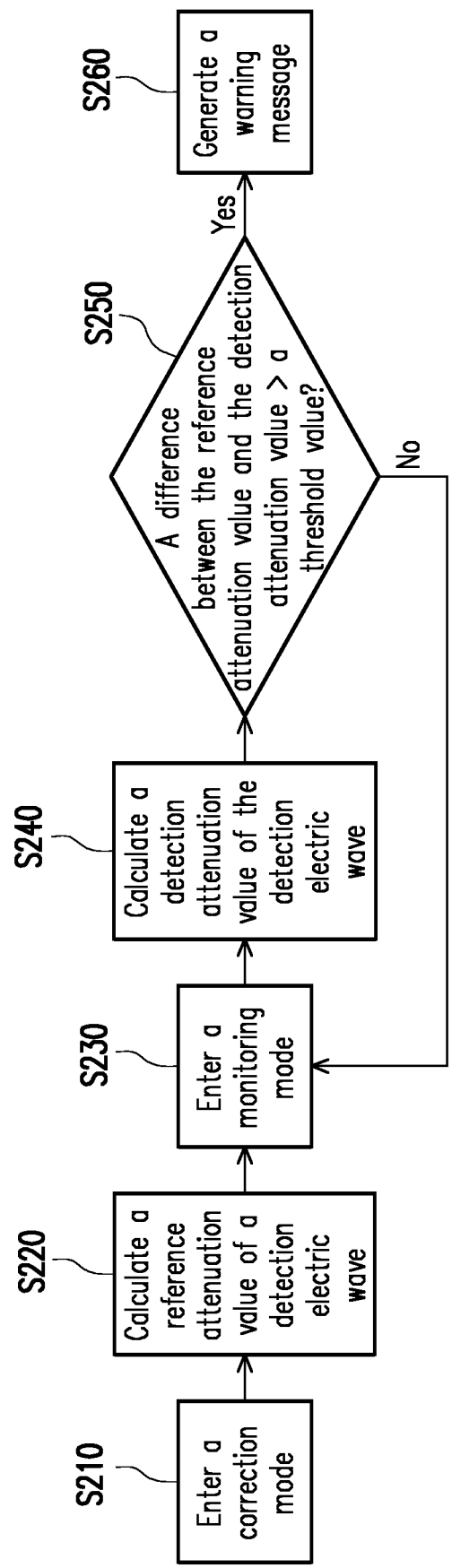
FIG. 2 is a flowchart of a gas detection operation according to an embodiment of the invention.

Based on the above description, the equipment terminal UE1 of the embodiment of the invention may receive the transmission electric wave RS1. In view of an operation detail, referring to FIG. 1 and FIG. 2, where FIG. 2 is a flowchart of a gas detection operation according to an embodiment of the invention. First, a correction mode of an initializing operation is entered (S210). When the medium 110 includes a normal gas composition, the application terminal AP1 may send the detection electric wave TS1. The equipment terminal UE1 is configured to receive the transmission electric wave RS1, and calculates a difference between strength values of the transmission electric wave RS1 and the detection electric wave TS1, so as to calculate a reference attenuation value of the detection electric wave TS1 generated during a transmission process in a step S220. It should be noted that a magnitude of the strength value of the detection electric wave TS1 may be pre-stored in the equipment terminal UE1; or the application terminal AP1 may mount related information of the strength value of the detection electric wave TS1 in the detection electric wave TS1 in form of a data packet. The equipment terminal UE1 may decode the received transmission electric wave RS1 to acquire the strength value of the detection electric wave TS1.

After the above initializing operation is completed, the gas detection apparatus 100 enters a monitoring mode (step S230). In the monitoring mode, the application terminal AP1 may continuously sends the detection electric wave TS1, and the equipment terminal UE1 is configured to receive the transmission electric wave RS1. The transmission electric wave RS1 is generated by the detection electric wave TS1 after penetrating through the medium 110. Moreover, in a step S240, the equipment terminal UE1 calculates a detection attenuation value of the detection electric wave TS1 generated in the transmission process according to the transmission electric wave RS1.

It should be noted that if a gas composition of the medium 110 in the monitoring mode is similar to the gas composition of the medium 110 in the correction mode, the reference attenuation value and the detection attenuation value calculated by the gas detection apparatus 100 are close to each other. In contrast, when the gas composition of the medium 110 is changed to cause increase of an attenuation amount of the electric wave in the monitoring mode, the reference attenuation value and the detection attenuation value calculated by the gas detection apparatus 100 have a certain difference, i.e., the detection attenuation value is greater than the reference attenuation value by a offset value. Based on the above description, in a step S250, a difference between the reference attenuation value and the detection attenuation value is calculated, and it is determined whether the difference between the reference attenuation value and the detection attenuation value is greater than a predetermined threshold value. When the difference between the reference attenuation value and the detection attenuation value is greater than the threshold value, a step S260 is executed to send a warning message. In contrast, if the difference between the reference attenuation value and the detection attenuation value is not greater than the threshold value, the flow returns to the step S230 to continue the monitoring mode.

It should be noted that in the embodiment, in the space 101, the detection electric wave TS1 generated by the single application terminal AP1 may be plural (each representing a different direction angle), and the transmission electric wave RS1 generated according to the detection electric waves TS1 may also be plural. In this case, the equipment terminal UE1 may receive a plurality of the transmission electric waves RS1 generated according to the detection electric waves TS1. Therefore, in the correction mode, the equipment terminal UE1 may acquire a plurality of reference attenuation values, and in the monitoring mode, the equipment terminal UE1 may acquire a plurality of detection attenuation values.

Under such condition, in case of the monitoring mode, the equipment terminal UE1 may select one of the reference attenuation values to execute the step S250, and select one of the detection attenuation values to execute the step S250. To be specific, the equipment terminal UE1 may select the maximum one of the reference attenuation values and the maximum one of the detection attenuation values to execute the step S250, and calculate the difference between the reference attenuation value and the detection attenuation value. In another embodiment of the invention, the equipment terminal UE1 may also select N relatively large reference attenuation values in the plurality of reference attenuation values, and calculate an average thereof to serve as the reference attenuation value used in execution of the step S250, and also select N relatively large detection attenuation values in the plurality of detection attenuation values, and calculate an average thereof to serve as the detection attenuation value used in execution of the step S250, where N is a positive integer greater than 1.

In the above description, N may be set by a designer, which is not limited by the invention.

The reference attenuation value and the detection attenuation value may be obtained by calculating a value of a Received Signal Strength Indication (RSSI) of the transmission electric wave RS1. The RSSI is a negative decibel (dB) value, which is used for representing a value of a radio frequency wave. The stronger a signal of the radio frequency wave is, the better the connection quality is. Therefore, the more the RSSI is close to 0, the stronger the corresponding electric wave strength is.

It should be noted that in the embodiment of the invention, the number of the application terminal AP1 may be plural, and the number of the equipment terminal UE1 may also be plural. By configuring a plurality of the application terminals AP1 and the equipment terminals UE1, between the application terminals AP1 and the equipment terminals UE1, transmission channels constructed between the detection electric waves TS1 and the transmission electric waves RS1 may have higher distribution density in the medium 110, which further improves integrity of the gas detection and accuracy of the detection result.

It should be noted that when the gas detection apparatus 100 has a plurality of the application terminals AP1, each of the application terminals AP1 may add an identification signal to the transmitted detection electric wave TS1. In this way, the equipment terminal UE1 may decode the identification signal in the transmission electric wave RS1 to learn the application terminal AP1 corresponding to the transmission electric wave RS1. In this way, the equipment terminal UE1 may generate the reference attenuation value and the sensing attenuation value corresponding to the correct application terminal AP1, and generate the correct detection result.

Figure 3A:
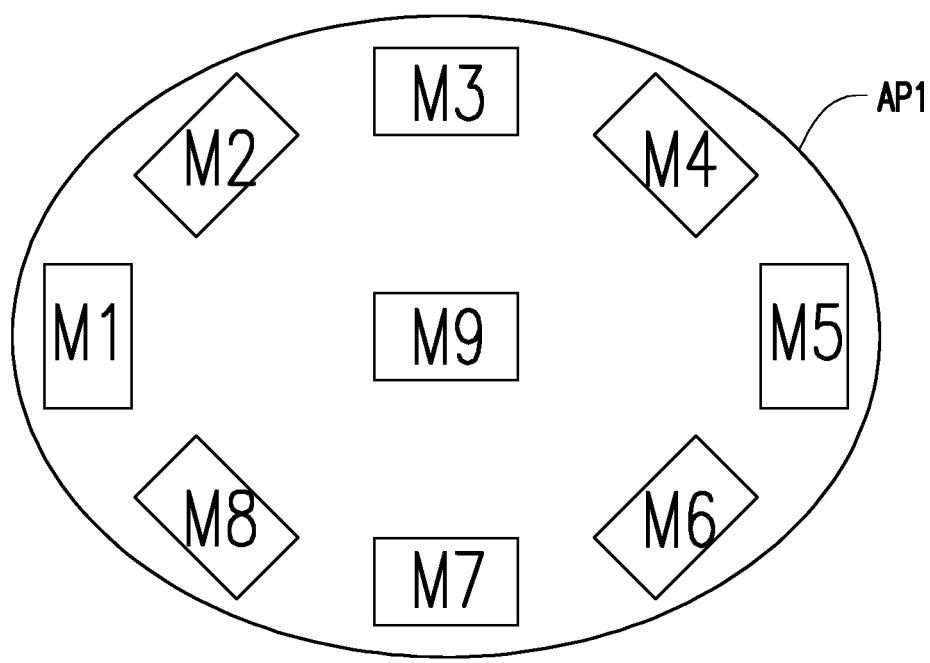
FIG. 3A and FIG. 3B are schematic diagrams of an implementation of an application terminal according to an embodiment of the invention.
Figure 3B:
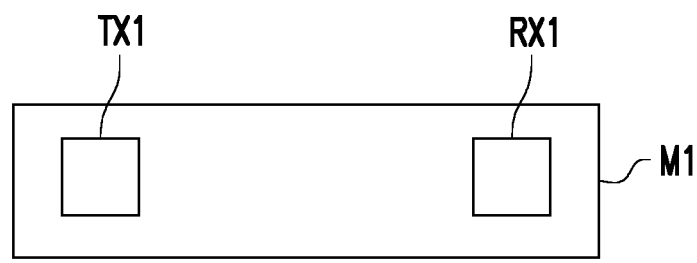

Referring to FIG. 3A and FIG. 3B, FIG. 3A and FIG. 3B are schematic diagrams of an implementation of the application terminal according to an embodiment of the invention. In FIG. 3A, the application terminal AP1 includes a plurality of element groups M1-M9. In FIG. 3B, the element group M1 is taken as an example and illustrated, and the element group M1 includes an electric wave emitting element TX1 and an electric wave receiving element RX1. The application terminal AP1 may send the detection electric wave through the electric wave emitting element TX1. Moreover, the application terminal AP1 may also receive the electric waves through the electric wave receiving element RX1, so as to communicate with the other application terminals and the equipment terminals in the space.

It should be noted that the equipment terminal of the embodiment of the invention may have a same hardware framework with that of the application terminal AP1. Namely, in case of the equipment terminal configuration, the electric wave receiving element RX1 may be used for receiving the transmission electric wave and generating the detection result.

In the embodiment, the application terminal AP1 further includes a controller (not shown) to execute necessary calculation operations.

In the embodiment of the invention, the element groups M1-M9 may be disposed at a plurality of positions of the application terminal AP1. For example, the element groups M1-M9 may be disposed around the application terminal AP1, and the element group M9 is disposed at a center of the application terminal AP1. When the application terminal is set on a ceiling of an indoor space, the application terminal AP1 may send a plurality of detection electric waves to the surrounding and below through the element groups M1-M9.

In order to improve practicability of the gas detection apparatus 100, the application terminals AP1 may be disposed in collaboration with indoor electrical devices. For example, light-emitting diodes may be configured in the application terminals AP1 to form lamps. By disposing a plurality of the application terminals AP1 in a plurality of corners of a room, besides a lighting function, an integral detection operation to the gas in the room space may be performed.

In other embodiments of the invention, the application terminals AP1 may also be disposed in collaboration with smoke detectors. Alternatively, the application terminals AP1 may also be disposed in collaboration with electrical devices such as an air conditioner, an electric fan, etc., which is not limited by the invention.

Moreover, in the embodiment of the invention, the equipment terminals UE1 may be disposed in various types of electronic devices such as a desktop computer, a notebook computer, a tablet computer, a mobile phone or other types of electronic devices, which is not limited by the invention.

Figure 4:
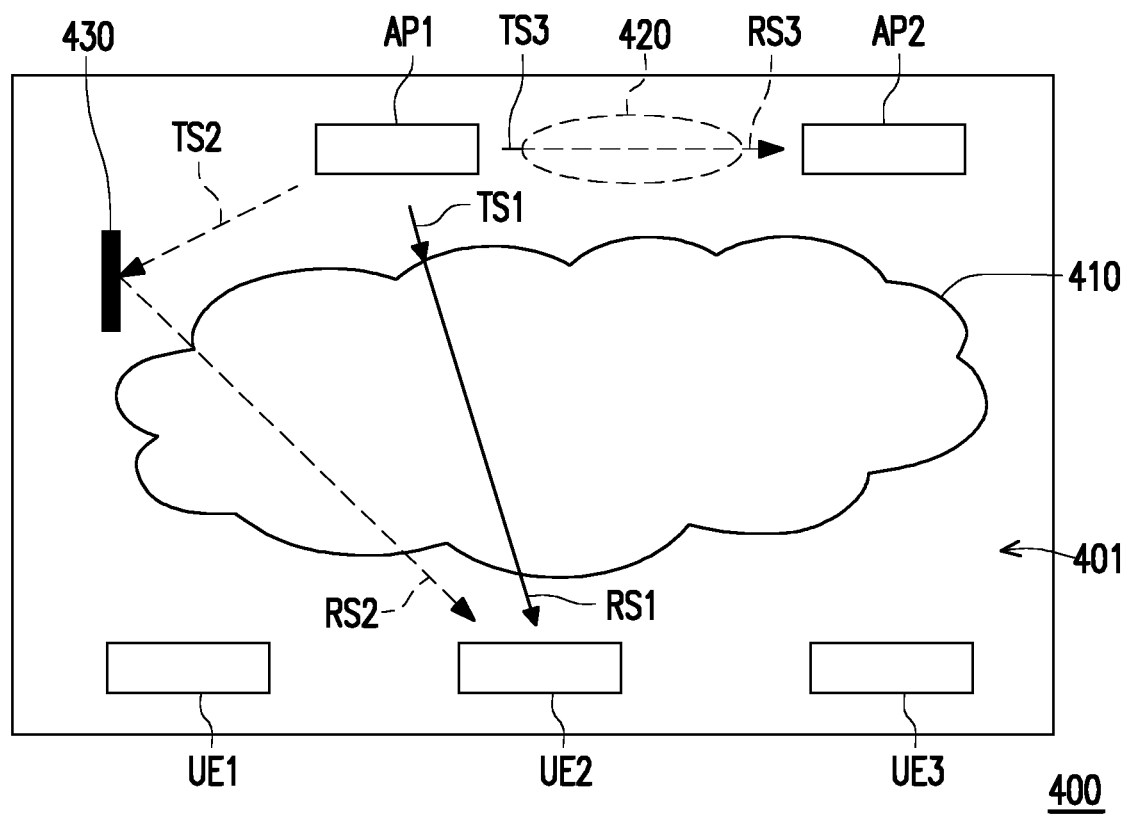
FIG. 4 is a schematic diagram of a gas detection device according to another embodiment of the invention.

Referring to FIG. 4, FIG. 4 is a schematic diagram of a gas detection device according to another embodiment of the invention. The gas detection apparatus 400 includes application terminals AP1-AP2 and equipment terminals UE1-UE3. The application terminals AP1-AP2 are used for respectively sending a plurality of detection electric waves (for example, detection electric waves TS1 and TS2), and the detection electric waves penetrate through a medium 410 and/or 420. The equipment terminals UE1-UE3 are used for receiving transmission electric waves (for example, transmission electric waves RS1 and RS2) generated according to the detection electric waves (for example, the detection electric waves TS1 and TS2), and perform the gas detection operation according to the received transmission electric waves.

In the embodiment, the application terminal (for example, the application terminal AP2) may also be configured as the equipment terminal, and is used for receiving the transmission electric wave RS3 generated according to the detection electric wave TS3 sent by the application terminal AP1. The detection electric wave TS3 penetrates through the gas (the medium 420) between the application terminals AP1 and AP2, and the application terminal AP2 configured as the equipment terminal detects a gas state of the medium 420 according to the received transmission electric wave RS3.

Referring to FIG. 4, FIG. 5A and FIG. 5B synchronously, where FIG. 5A and FIG. 5B are flowcharts of a gas detection operation according to another embodiment of the invention. In FIG. 5A, the correction mode is entered in a step S510, and a detection operation is started in a step S511, and the application terminals AP1-AP2 send the detection electric waves TS1 and TS2. Then, in a step S512, one of the equipment terminals UE1-UE3 is elected to serve as an electric wave receiving element, and the selected electric wave receiving element receives the transmission electric waves RS1 and RS2 generated according to the detection electric waves TS1 and TS2. As shown in FIG. 4, the detection electric wave TS1 may directly penetrate through the medium 410 to generate the transmission electric wave RS1, and the equipment terminal UE1 receive the transmission electric wave RS1. The detection electric wave TS2 is reflected by a reflector 430 in the space 401 to penetrate through the medium 410 to generate the transmission electric wave RS2. Then, the equipment terminal UE1 receives the transmission electric wave RS2. Namely, in the embodiment, the single electric wave receiving element of the equipment terminal UE1 probably receives a plurality of transmission electric waves. Based on the above description, the equipment terminal reads transmission delays of the received transmission electric waves in a step S513, and determines the transmission electric wave with the minimum transmission delay in a step S514.

Further, when the application terminal AP1 sends the detection electric waves TS1 and TS2, the application terminal AP1 may add identification information to the detection electric waves TS1 and TS2. The identification information is used for informing the receivers (the equipment terminals UE1-UE3) that the detection electric waves TS1 and TS2 are sent by a specific electric wave emitting element of the application terminal AP1. In this way, the equipment terminal (for example, the equipment terminal UE1) may determine the detection electric wave with the minimum transmission delay time in the detection electric waves TS1 and TS2 according to receiving time points of the transmission electric waves RS1 and RS2 of the same emitting source. As shown in FIG. 4, a transmission path of the detection electric wave TS1 to the transmission electric wave RS1 is the shortest, so that the transmission delay time of the detection electric wave TS1 may be a selected transmission delay time.

In a step S515, the equipment terminal (for example, the equipment terminal UE1) records a strength value of the transmission electric wave (for example, the transmission electric wave RS1) corresponding to the selected transmission delay time to serve as a reference strength value.

Then, in FIG. 5B, the monitoring mode is entered in a step S520. In a step S521, a periodic detection operation is activated, and the application terminals AP1 and AP2 periodically send the detection electric waves. In the embodiment, emission periods of the detection electric waves may be determined by a designer, which is not limited by the invention.

Then, in a step S522, one of the equipment terminals UE1-UE3 is selected as the electric wave receiving element to receive the transmission electric wave, and in a step S523, a transmission delay time of the detection electric wave is read to perform transmission loss compensation of the detection electronic wave. The transmission loss compensation executed in the step S523 may be implemented through the transmission loss compensation method well known by those skilled in the art, which is not limited by the invention.

In a step S524, it is determined whether all of the electric wave receiving elements are ever selected, and if yes, a step S525 is executed, and if not, the step S522 is executed to select anther electric wave receiving element to execute the step S523.

Based on the above description, each of the equipment terminals UE1-UE3 records signal strength value of a plurality of transmission electric waves (for example, the transmission electric waves RS1 and RS2) through the step S525, and in a step S526, a difference between the reference strength value and each of the signal strength values is calculated. In a step S527, it is determined whether the above difference is greater than a predetermined threshold value, and when the difference is greater than the threshold value, in a step S528, it is determined that the gas has an abnormal state. In contrast, when the difference is not greater than the threshold value, the step S520 is re-executed to continue the monitoring operation.

In the embodiment, when it is determined that the gas has the abnormal state in the step S528, the equipment terminal (for example, the equipment terminal UE1) may send a warning message. The warning message may be a sound, a vibration or a text message, which is not limited by the invention. Moreover, the equipment terminal UE1 may transmit the warning message to a remote electronic device through a wired or wireless communication manner. In this way, a supervisor may detect the gas in the space through a remote monitoring method, and adopt a corresponding measure when the gas has the abnormal state.

In summary, in the invention, by transmitting the detection electric waves in the space, and calculating attenuation of the detection electric waves generated in the transmission channel, it is detected whether the gas state in the space is abnormal. In this way, detection of the gas state is not confined to a part of the space. Moreover, the gas detection apparatus of the embodiment of the invention may be integrated with electrical devices in the space to achieve the gas detection effect under a condition of not influencing aesthetics.

It will be apparent to those skilled in the art that various modifications and variations can be made to the disclosed embodiments without departing from the scope or spirit of the invention. In view of the foregoing, it is intended that the invention covers modifications and variations provided they fall within the scope of the following claims and their equivalents.

What is claimed is:

1. A gas detection apparatus, comprising:
   at least one application terminal, sending a plurality of detection electric waves; and
   at least one equipment terminal, configured to receive a plurality of transmission electric waves respectively generated according to the detection electric waves, wherein the at least one equipment terminal is configured to:
      calculate a plurality of reference attenuation values of the transmission electric waves in a correction mode by calculating a difference between strength values of the transmission electric waves and strength values of the detection electric waves, wherein the strength values of the detection electric waves are pre-stored in the at least equipment terminal or included in the detection electric waves in form of a data packet;
      calculate a plurality of detection attenuation values of the transmission electric waves in a monitoring mode; and
      generate a detection result by comparing the reference attenuation values with the detection attenuation values.

2. The gas detection apparatus as claimed in claim 1, wherein the at least one equipment terminal calculates a difference between one of the reference attenuation values and one of the detection attenuation values, and generates a detection signal indicating gas abnormity when the difference is greater than a predetermined threshold value.

3. The gas detection apparatus as claimed in claim 2, wherein the at least one equipment terminal generates the detection signal indicating gas normality when the difference is not greater than the predetermined threshold value.

4. The gas detection apparatus as claimed in claim 1, wherein the at least one application terminal comprises:
   a plurality of electric wave emission elements, disposed at a plurality of positions of the application terminal, and respectively emitting the detection electric waves according to a plurality of emission directions.

5. The gas detection apparatus as claimed in claim 1, wherein the at least one equipment terminal comprises:
   a plurality of electric wave receiving elements, configured to receive the transmission electric waves.

6. A gas detection apparatus, comprising:
   at least one application terminal, sending a plurality of detection electric waves; and
   at least one equipment terminal, configured to receive a plurality of transmission electric waves generated according to the detection electric waves, wherein the at least one equipment terminal is configured to:
      calculate a plurality of transmission delay times of the transmission electric waves in a correction mode, and calculate the minimum one of the transmission delay times to obtain a selected transmission delay time, and record a reference strength value of the transmission electric wave corresponding to the selected transmission delay time; and
      calculate and record a plurality of signal strength values of the transmission electric waves in a monitoring mode, calculate a plurality of differences between the reference strength value and the signal strength values, and generate a detection result according to the differences.

7. The gas detection apparatus as claimed in claim 6, wherein in the monitoring mode, when the at least one equipment terminal calculates that one of the differences is greater than a predetermined threshold value, the at least one equipment terminal generates a sensing signal indicating gas abnormity.

8. The gas detection apparatus as claimed in claim 7, wherein in the monitoring mode, when the at least one equipment terminal calculates that the differences are all not greater than the predetermined threshold value, the at least one equipment terminal generates the sensing signal indicating gas normality.

9. The gas detection apparatus as claimed in claim 6, wherein the at least one equipment terminal comprises:
   a plurality of electric wave receiving elements, configured to receive the transmission electric waves.

10. The gas detection apparatus as claimed in claim 9, wherein in the monitoring mode, a plurality of electric wave emission elements in the at least one application terminal are sequentially selected to emit the detection electric waves, the at least one equipment terminal obtains a plurality of transmission channel losses of the transmission electric waves according to the transmission delay times, and compensates the signal strength values of the transmission electric waves according to the transmission channel losses.

11. The gas detection apparatus as claimed in claim 10, wherein in the monitoring mode, the at least one application terminal sequentially sends the detection electric waves according to a detection period.

12. The gas detection apparatus as claimed in claim 6, wherein the at least one application terminal comprises:
    a plurality of electric wave emission elements, disposed at a plurality of positions of the application terminal, and respectively emitting the detection electric waves according to a plurality of emission directions.

* * * * *